US009545297B1

(12) United States Patent
Krastev

(10) Patent No.: US 9,545,297 B1
(45) Date of Patent: Jan. 17, 2017

(54) DENTAL IMPLANT SURGERY ORGANIZER CASE

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 0 days.

(21) Appl. No.: 13/959,963

(22) Filed: Aug. 6, 2013

Related U.S. Application Data

(60) Provisional application No. 61/692,789, filed on Aug. 24, 2012.

(51) Int. Cl.
*A61C 19/10* (2006.01)
*A61J 1/00* (2006.01)
*B65D 21/02* (2006.01)

(52) U.S. Cl.
CPC .............. *A61C 19/10* (2013.01); *A61J 1/00* (2013.01); *B65D 21/0201* (2013.01)

(58) Field of Classification Search
CPC ............ A47B 53/00; A47B 87/00; A61J 1/03; A61J 7/04; B65D 21/02; B65D 21/0201
USPC .... 206/369, 446, 443, 459.5; 220/4.21–4.24, 220/23.2, 23.4, 23.8; 211/76
See application file for complete search history.

(56) References Cited

U.S. PATENT DOCUMENTS

| 364,623 A | 6/1887 | Beidler |
| 1,659,333 A * | 2/1928 | Roberts ........................... 211/76 |
| 2,383,367 A | 8/1945 | Brown |
| 3,033,355 A | 5/1962 | Van Sickle |
| 3,269,788 A * | 8/1966 | Kneer ........................... 312/200 |
| 3,324,996 A | 6/1967 | Jordt |
| 3,397,671 A | 8/1968 | Hartman, Jr. |
| 3,402,850 A | 9/1968 | Barton |
| 3,407,454 A | 10/1968 | Myatt |
| 3,630,171 A | 12/1971 | Huck |
| 3,975,803 A | 8/1976 | Katayama |
| 4,026,588 A | 5/1977 | Bisbing |
| 4,038,937 A | 8/1977 | Moe |
| 4,057,309 A * | 11/1977 | Fragale ........................ 312/290 |
| 4,084,695 A | 4/1978 | Halbich |

(Continued)

FOREIGN PATENT DOCUMENTS

EP 2 564 798 6/2013
GB 2 418 421 3/2006

*Primary Examiner* — Andrew Perreault
(74) *Attorney, Agent, or Firm* — Thomas A. O'Rourke; Bodner & O'Rourke, LLP

(57) ABSTRACT

A dental implant organizer case includes a housing with a plurality of compartments selectively arranged therein. Each compartment includes: a respective lid pivotally mounted to the housing to cover the compartment's cavity when closed; means for biasing the lid from the closed to the open position; means to releasably secure the lid in the closed position; means to releasably support dental implant containers within the compartment, in an upright position; and a respective tooth number marking to indicate the tooth intended for the implant containers therein. The selectively arranged compartments may form a semi-circular or an in-line arrangement. Two compartment levels may be utilized, with the lower compartments being accessible using a tray being slidable with respect to the housing. Two cases may be secured together to be pivotable between collapsed and extended positions, where the first and second cases store dental implant containers for left-hand and right-hand teeth, respectively.

20 Claims, 17 Drawing Sheets

(56) References Cited

U.S. PATENT DOCUMENTS

| | | | |
|---|---|---|---|
| 4,294,348 A | 10/1981 | Hastings | |
| 4,318,477 A | 3/1982 | Kerpe | |
| 4,372,445 A | 2/1983 | Keffeler | |
| 4,593,819 A | 6/1986 | Will | |
| 4,735,318 A | 4/1988 | Keffeler | |
| 4,793,492 A | 12/1988 | Halbich | |
| 4,817,819 A | 4/1989 | Kelly | |
| 4,872,559 A | 10/1989 | Schoon | |
| 4,893,722 A * | 1/1990 | Jones | B65F 1/006 220/23.83 |
| 4,951,832 A * | 8/1990 | Tenney | B65D 21/02 206/505 |
| 4,966,599 A | 10/1990 | Pollock | |
| 4,997,090 A * | 3/1991 | Lenmark et al. | 206/570 |
| 4,998,623 A | 3/1991 | Doull | |
| 5,011,018 A | 4/1991 | Keffeler | |
| 5,109,984 A | 5/1992 | Romick | |
| 5,174,451 A | 12/1992 | Niven | |
| 5,267,650 A * | 12/1993 | Gilbilisco | 206/534 |
| 5,348,158 A | 9/1994 | Honan | |
| 5,553,712 A | 9/1996 | Tisbo | |
| 5,558,229 A | 9/1996 | Halbich | |
| 5,575,399 A | 11/1996 | Intini | |
| 5,579,941 A | 12/1996 | Romick | |
| 5,735,406 A | 4/1998 | Keffeler | |
| 5,833,072 A | 11/1998 | Lambelet, Jr. | |
| 5,878,757 A | 3/1999 | Hernandez | |
| 5,890,613 A * | 4/1999 | Williams | 220/23.4 |
| 6,021,901 A | 2/2000 | Wolfe | |
| 6,328,746 B1 | 12/2001 | Gambale | |
| 6,471,060 B1 | 10/2002 | Leyshon | |
| 6,564,945 B1 * | 5/2003 | Weinstein et al. | 206/531 |
| 6,758,338 B2 | 7/2004 | Lien | |
| 6,779,663 B1 | 8/2004 | Pocsi | |
| 6,959,806 B2 | 11/2005 | Barker | |
| 7,004,324 B1 | 2/2006 | Delorio | |
| 7,097,037 B1 | 8/2006 | Keffeler | |
| 7,158,011 B2 | 1/2007 | Brue | |
| 7,228,966 B1 | 6/2007 | Turner | |
| 7,367,451 B2 | 5/2008 | Pendergraph | |
| 7,497,351 B2 | 3/2009 | Amundson | |
| 7,624,890 B2 | 12/2009 | Noble | |
| 7,793,785 B2 | 9/2010 | Keffeler | |
| 7,877,268 B2 | 1/2011 | Kulkarni | |
| 2003/0159319 A1 * | 8/2003 | Ransom et al. | 40/306 |
| 2004/0089581 A1 | 5/2004 | Dienst | |
| 2007/0062964 A1 * | 3/2007 | Kampf et al. | 220/835 |
| 2009/0281657 A1 | 11/2009 | Gak | |
| 2013/0026056 A1 * | 1/2013 | Key | 206/459.5 |
| 2014/0021086 A1 | 1/2014 | Roesler | |
| 2014/0251862 A1 | 9/2014 | Priebe | |

\* cited by examiner

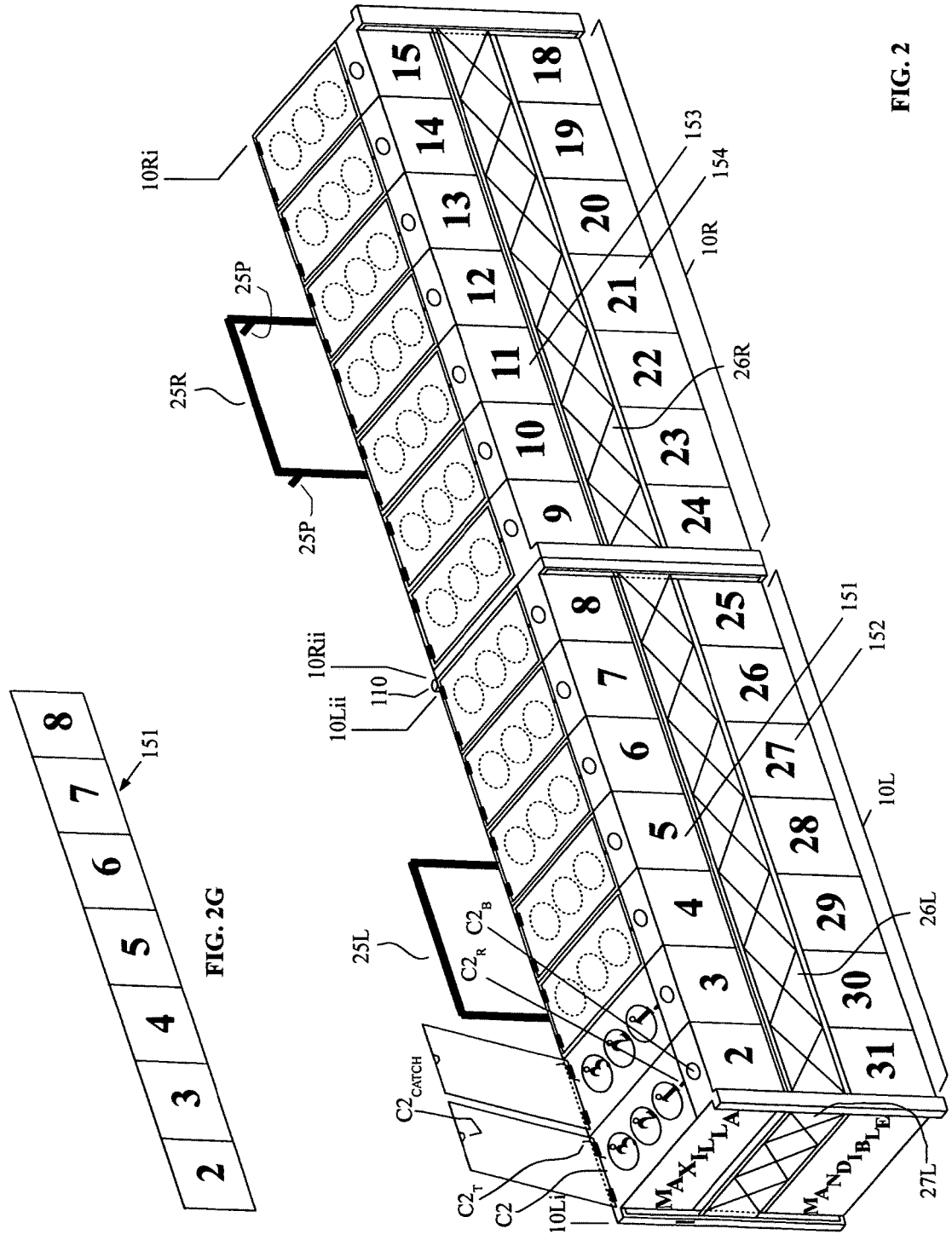

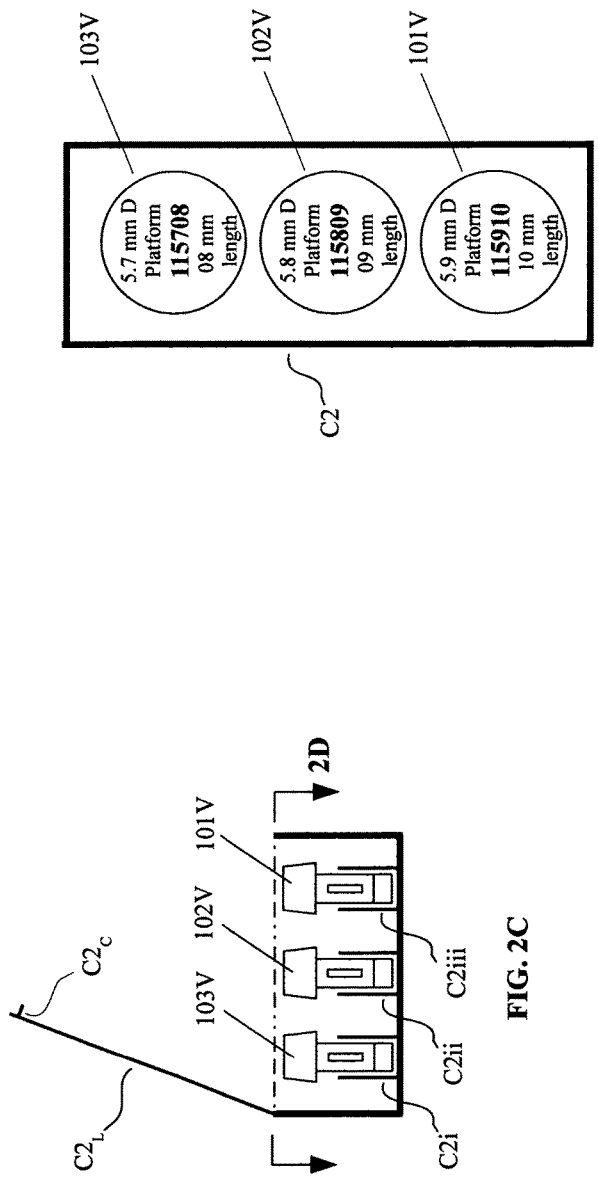
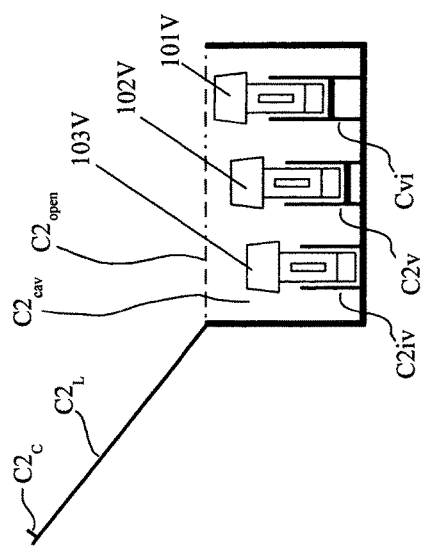
FIG. 2D
FIG. 2C
FIG. 2F

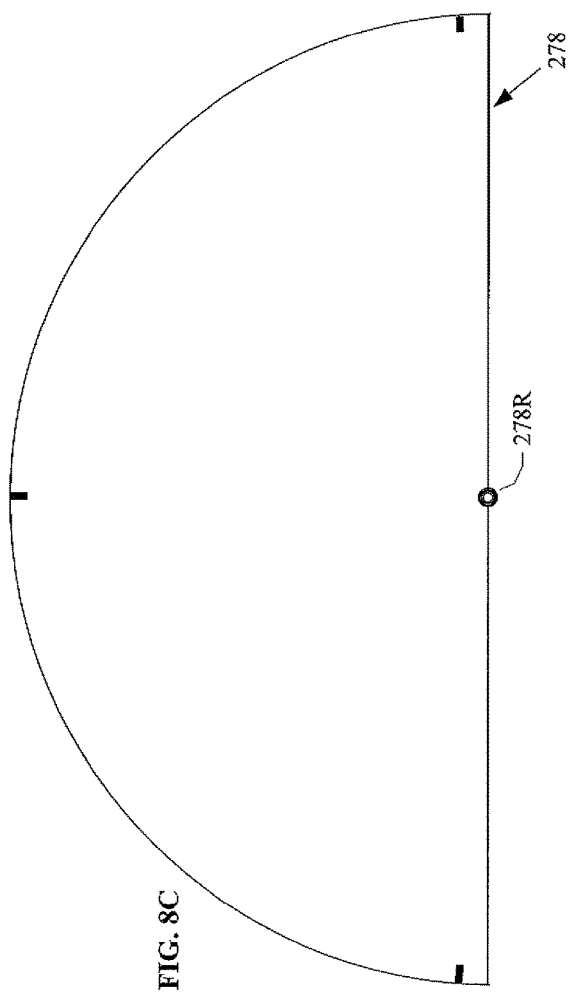
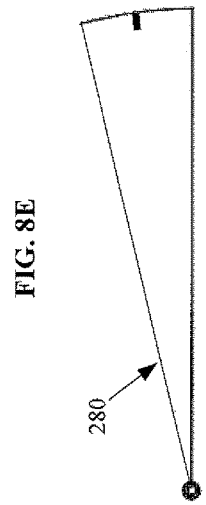
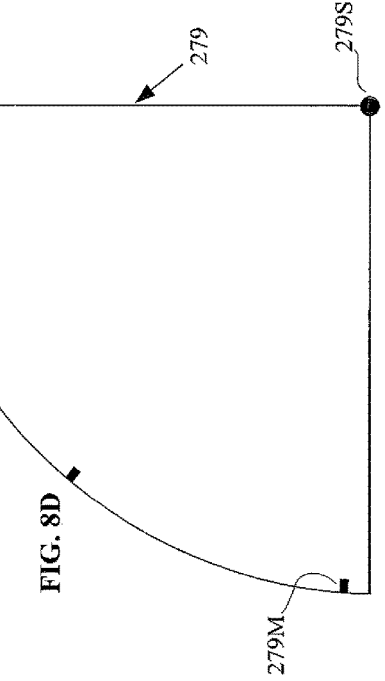

DENTAL IMPLANT SURGERY ORGANIZER CASE

CROSS REFERENCES TO RELATED APPLICATIONS

This application claims priority on U.S. Provisional Application Ser. No. 61/692,789, filed on Aug. 24, 2012, the disclosures of which are incorporated herein by reference.

FIELD OF THE INVENTION

The present invention relates to improvements in dental implant surgery, and more particularly to apparatus which is adapted to aid an oral surgeon in organizing implants for a patient's procedure, and to help prevent dropping of implants, to help increase the speed of the procedure, and to reduce the likelihood of the surgeon inadvertently deviating from the intended procedure by eliminating confusion as to which implant belongs in a given site.

BACKGROUND OF THE INVENTION

There are many conditions which may result in a person becoming partially or completely edentulous (periodontal disease, an injury, etc.), which in the past had been remedied by the wearing of a prosthetic device, known as dentures. Dentures were constructed to replace the missing teeth and were supported by surrounding teeth and/or by the underlying tissue. The significant drawbacks to the wearing of such partial or complete dentures, principally its means of support, which often required the use of adhesives, as well as its cleaning requirements, served to bolster the development of dental implants.

Today's dental implants are typically root form endosseous (in the bone), being a "root" device (a screw) that is usually made of titanium, and which is inserted into the jaw through the bone at the alveolar ridges. After a healing period, an abutment is attached thereto and may protrude through the periostium and receive a prosthodontic appliance—a new tooth.

It is not uncommon for an implant procedure to be performed on both the maxilla (upper jaw) and the mandible (lower jaw), and in some cases, enough titanium screws may be implanted to replace all of the missing teeth of a completely edentulous person. Although there need not be a corresponding implant screw for each prosthodontic tooth installed, and for the maxilla, where bone density is poorer than the lower jaw, the number of implants will depend on the quality and volume of bone at each prospective implant site. An oral surgeon will generally place 8-10 implants to support a complete set of 14 replacement teeth for the upper jaw. This is done when the final prosthetic device is fixed and only retrievable by the restorative dentist. The same applies to the lower jaw, but a full fixed case can be done with fewer implants, as the lower jaw is generally more favorable for implants in terms of its bone density. Generally, when fabricating a removable prosthesis that is implant supported, 6 implants are used in the upper jaw, and 2 or 4 implants are used in the lower anterior jaw. Each site will require individual preparation and an implant screw, referred to as a "platform," where the platform's diameter and length is optimum for the geometry of that particular site.

As a general rule, greater strength and better result are obtained for the subsequently installed prosthodontic teeth, by implanting the longest platform with the largest diameter that the bone is able to support locally. Because the physiology of the jaw bones normally varies at different locations throughout the mouth, a range of different size implants may be used at each location. In the front of the mouth, shorter and narrower implants are generally used, and often have diameters in the range of 3.5 mm to 4.2 mm. If a particular patient has an unusually narrow space between two teeth, a "mini dental implant," being in the range of 2 mm to 3.5 mm, may be used. Towards the back of the mouth, the bone that supports the molars may require implants diameters in the range of 4.5 mm to 6.0 mm, as that is where the strength of the tooth is crucial for mastication. For a full technical discussion of the rationale for particular implant platform sizing, see Contemporary Implant Dentistry, by Carl E. Misch, $3^{rd}$ Ed., p. 160-177, the disclosures of which are incorporated herein by reference.

The surgeon may make a final selection for each implant platform during the procedure, depending upon final measurements taken of the bone after formation of the implant hole (osteotomy). Variations from a "recommended" platform size are frequently necessary, especially if a "spinner" occurs, which is an implant that does not have good primary fixation. In that case, a wider implant fixture must be placed to achieve proper primary stability. Therefore, the number of different sized/shaped platforms that the oral surgeon may need to have readily available during a procedure, to accommodate all of the implant sites, may often become considerable and unwieldy.

The concerns regarding the health and safety of the dental implant patient are as significant as with any other surgery being performed today. The dental implant surgeon is concerned with many things, including infection at the site of the implant, the potential injury/damage to surrounding blood vessels or teeth, the possibility of nerve damage, the potential for sinus problems when the platform protrudes into one of the sinus cavities, as well as the potential for loss of an implant or fracturing of a patients jaw. The diligent oral surgeon performing implant procedures is thus confronted by an array of issues that must be successfully negotiated in order to meet the accepted standard of practice, many of which principally relate to forming an optimally sized implant hole (osteotomy) for installation of the optimally sized platform (optimal length and width of the implant).

Where the patient requires multiple platforms to be implanted, and with the probability of needing to vary the platform selected for implantation from the "recommended" platform size, the potential for an error resulting in malpractice escalates. Furthermore, increased handling of the vials that contain the platform in a sterile environment also introduces the likelihood of its mishandling, which may result in dropping of the vial and ruining of the sterile seal, which would necessitate the use of a new implant, at additional cost.

The current invention seeks to organize the array of implants that may be used during surgery. The current invention allows an oral surgeon to be well prepared prior to surgery and during the surgery for any deviation from a planned implant size.

OBJECTS OF THE INVENTION

It is an object of the invention to provide a means of organizing dental implant platforms for an oral surgeon.

It is another object of the invention to provide a case that sorts dental implant platforms according to their use in the maxilla and/or the mandible.

It is a further object of the invention to provide a case that sorts dental implant platforms according to their use in respective tooth locations for both the maxilla and the mandible.

It is another object of the invention to provide a series of appropriate back-up implants.

It is a further object of the invention to properly orient the surgeon during the surgery, and eliminate confusion, as to the planned implant sites for a set of platforms.

It is another object of the invention to provide a means of visually identifying the intended tooth/jaw location for each of the dental implants stored in a case.

It is also an object of the invention to provide a means of collapsing a dental implant case for its transport or storage, and for expanding the case for more advantageous use during an implant procedure.

Further objects and advantages of the invention will become apparent from the following description and claims, and from the accompanying drawings.

SUMMARY OF THE INVENTION

A dental implant surgery organizer case is disclosed for organizing the multitude of implant platforms that may need to be readily available to an oral surgeon during the performance of implant procedures. The dental implant organizer may comprise an elongated left-side case being pivotally attached to an elongated right-side case, where the left-side case and the right-side case may pivot 180 degrees relative to each other, between a collapsed position, in which they are parallel but side-by-side with each other, and an extended position, in which they are parallel, but in line with each other. When occupying the collapsed position, the left-side case and the right-side case may be secured, on the ends opposite from the hinge, using a twist lock and pivotable flange.

Each case may be segregated by a plurality of walls into a series of compartments, and may preferably have seven compartments that are accessible from the top of the case. Each compartment may be adapted to support one or more implant platform vials. Each of the compartments may preferably support three or more such vials, which may contain the suggested implant platform and two other possible alternatively sized platforms that are likely to be needed by the surgeon as an alternate, depending upon quality and volume of the patient's bone at each prospective implant site. Each compartment may also preferably have a hinged lid that is biased into an open position, permitting easy access to the vials therein. The hinged lid may be retained in the closed position by a simple catch mechanism that may be actuated by the touching of a respective button on the top of the case. Each lid may preferably be translucent, to permit the practitioner or an assistant of the practitioner to recognize that an implant within the case has been utilized for a previous procedure, and that it needs to be replaced before using the case again.

The upper front of the left-side case may have a placard 151 (or have numbers stenciled thereon), to indicate tooth numbers for respective compartments, for the teeth of a patient's upper right side, which, in the American system, would principally be teeth numbers 2, 3, 4, 5, 6, 7, and 8 (wisdom tooth not included). In the European system (Palmer Notation method) they would be teeth numbers: 7, 6, 5, 4, 3, 2, and 1. The upper front of the right-side case may have a placard 153 (or have numbers stenciled thereon), to indicate the tooth numbers for respective compartments for the teeth of a patient's upper left side, which, in the American system, would principally be teeth numbers: 9, 10, 11, 12, 13, 14, and 15 (1, 2, 3, 4, 5, 6, and 7 in the European system). The lower front of the left-side case may have a placard 152 (or have numbers stenciled thereon), to indicate the tooth numbers for the teeth of a patient's lower right side, being teeth numbers: 31, 30, 29, 28, 27, 26, and 25 (7-1 in the European system). Finally, the lower front of the right-side case may have a placard 154 (or have numbers stenciled thereon), to indicate the tooth numbers for the teeth of a patient's lower left side, being teeth numbers: 24, 23, 22, 21, 20, 19, and 18 (1-7 in the European system).

A slidable shield may be received on the front of both the left-side case and the right-side case, each of which may be slid upward to conceal the teeth numbering for the maxilla, when the case is being used for implants on the patient's mandible, or it may be slid downward to conceal the teeth numbering for the mandible, when the case is being used for implants on the patient's maxilla. A placard or stenciling may also appear on the sides of the case identifying the upper numbering as being for the "MAXILLA," while the another placard or stenciling may identify the lower numbering as being for the "MANDIBLE." A slidable shield located on each end may be used to similarly conceal the MAXILLA" stencil when the case is being used for placing implants within the mandible, or vice versa.

In an alternative embodiment, the left-side case and the right-side case may each have a lower tray that is outwardly slidable with respect to the cases. Each lower tray may contain seven in-line compartments that may preferably support three or more vials, like the upper compartments previously described. Therefore, in this alternative embodiment, the upper compartments may be used to only organize vials of implant platforms for the teeth of the maxilla, while the lower compartments may be used to only organize vials of implant platforms for the teeth of the mandible.

Prior to performing an extensive implant procedure, the oral surgeon or assistant may position the case on a cart in proximity to the surgical chair, and pivot the left-side and right-side cases into the extended, in-line position. The trays may then be slid outwardly to expose the lower compartments. To further assist the surgeon during the procedure, the lids of only the tooth locations to receive implants may be unlatched, thereby permitting biasing of those lids into the open position. The surgeon will therefore have the correct assortment of tooth-specific implant platforms readily available to him/her during the procedure, along with a textual indication of which implant locations—tooth numbers and jaw position (maxilla/mandible)—which those platforms are intended for, to serve as a visual cue during the procedure to help prevent accidental mis-placement of an implant.

BRIEF DESCRIPTION OF THE DRAWINGS

FIG. 2 is the dental implant platform organizer case of FIG. 1, being shown in the extended, in-line position, for use during an implant procedure.

FIG. 2C is a side cross-sectional view of a compartment of the case of FIG. 2B, and is shown having support for three implant platform vials, which are shown stored therein.

FIG. 2D is a top view of the compartment of FIG. 2C.

FIG. 2F is the side cross-sectional view of FIG. 2C, but showing a multi-level support member for the implant platform vials.

FIG. 2G is a detail view of one of the placards used for the dental implant platform organizer case of FIG. 2.

FIG. 8C illustrates a first example of a rotator shield that is usable with the organizer case of FIG. 8A.

FIG. 8D illustrates a second example of a rotator shield that is usable with the organizer case of FIG. 8A.

FIG. 8E illustrates a third example of a rotator shield that is usable with the organizer case of FIG. 8A.

DETAILED DESCRIPTION OF THE INVENTION

Figure 1:
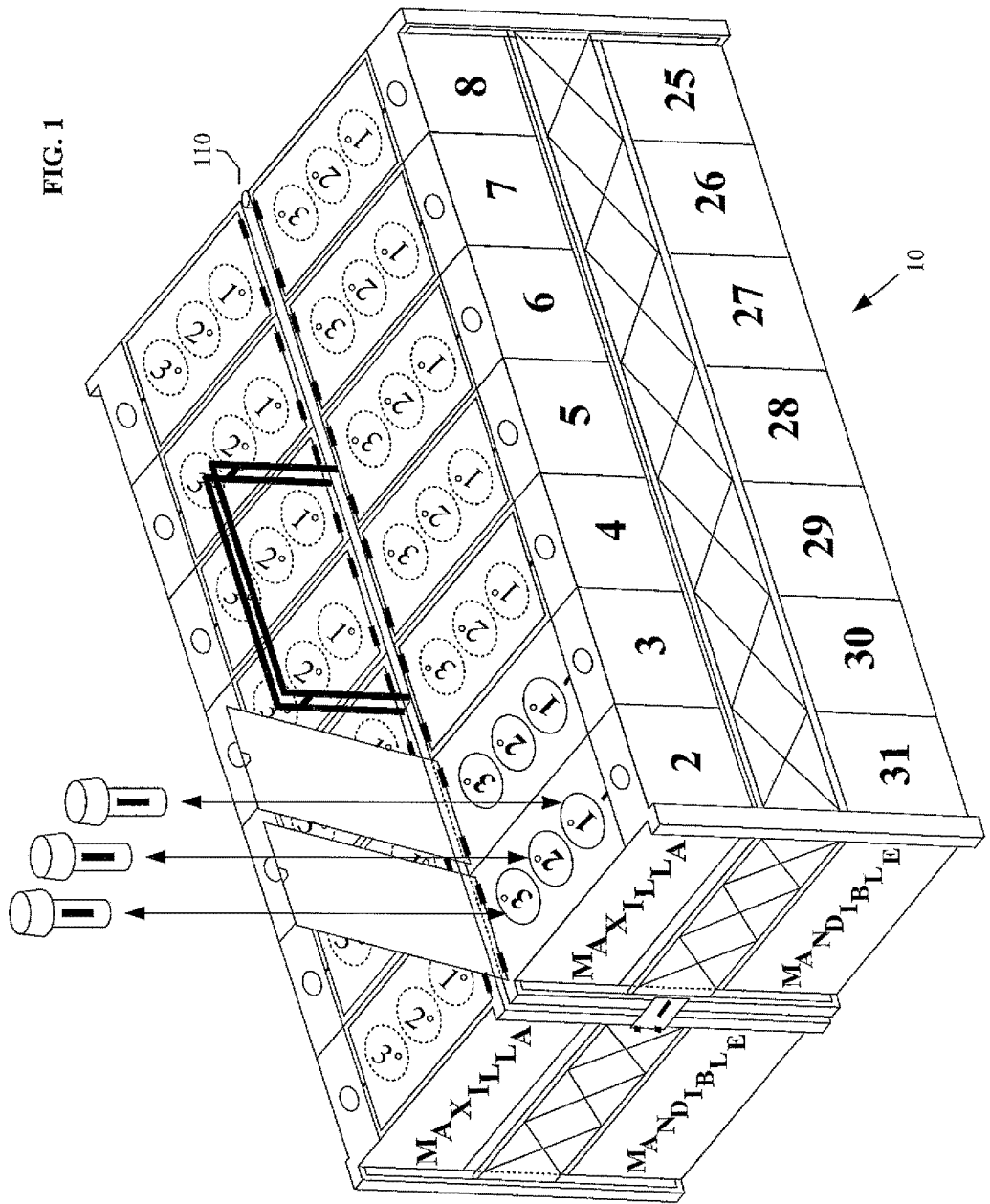
FIG. 1 is a first embodiment of the dental implant platform organizer case of the present invention, being shown in the collapsed position, which is preferable for storage/transport, but is also nonetheless usable during an implant procedure, particularly for a procedure performed on only the left-side or the right-side.
Figure 2A:
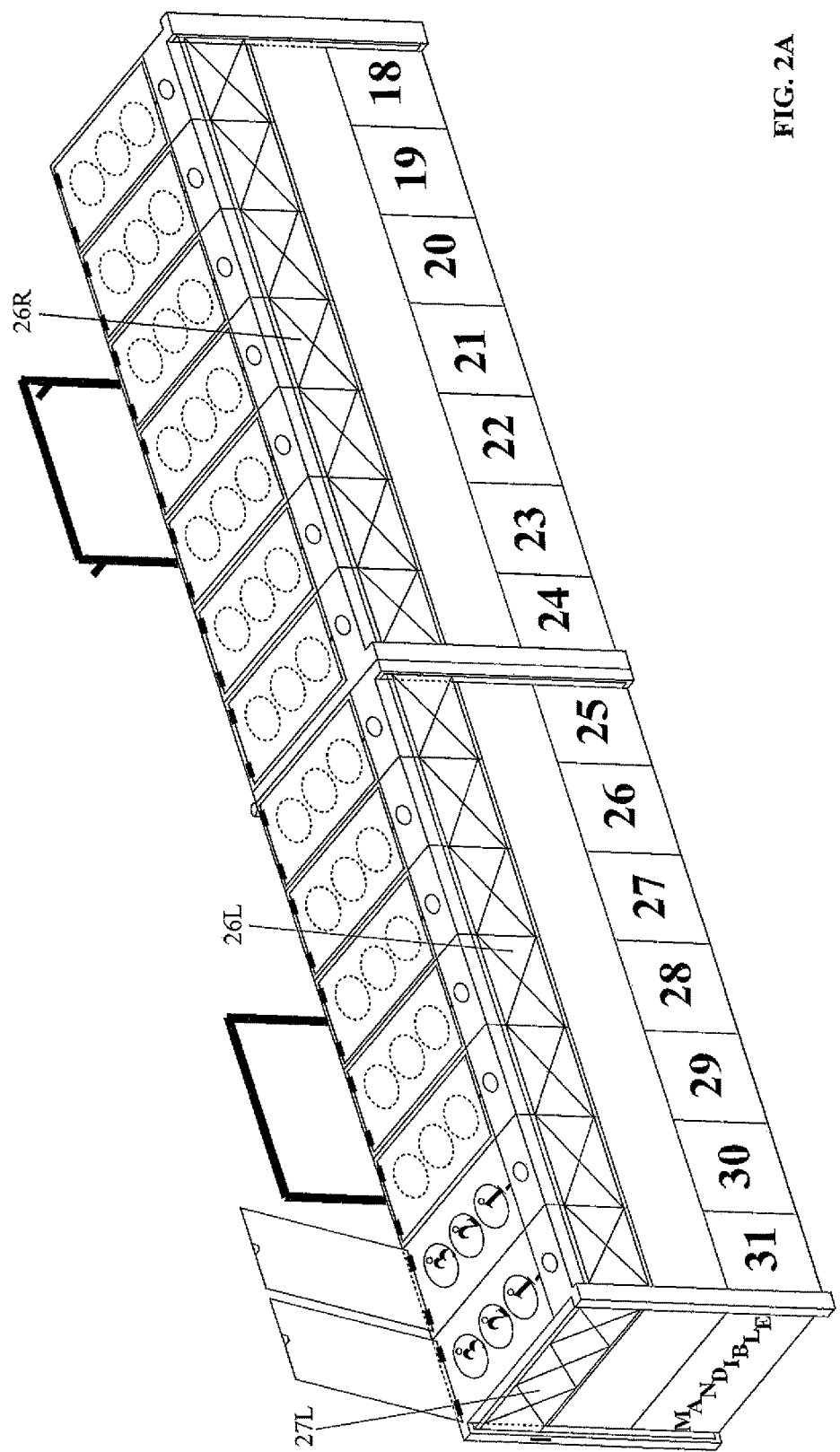
FIG. 2A is the dental implant platform organizer case of FIG. 2, being shown in the extended, in-line position for use during an implant procedure, and with its slidable shields having been slid upward to conceal the maxilla tooth numbers during a procedure requiring implants on the patient's mandible.

FIG. 1 shows a first embodiment of the dental implant organizer case 10 of the present invention, which serves to organize the multitude of implant platforms that may need to be readily available to an oral surgeon during the performance of implant procedures. As seen in FIG. 2, the dental implant organizer case 10 may comprise an elongated left-side case portion 10L being pivotally and/or releasably attached to an elongated right-side case portion 10R using hinge 110, where the left-side case portion and the right-side case portion may pivot 180 degrees relative to each other. Hinge 110, and its attachment to both the elongated left-side case 10L and the elongated right-side case 10R may permit the two cases to pivot between a collapsed position, in which they are parallel but side-by-side with each other (FIG. 1), and an extended position, in which they are parallel but in line with each other (FIG. 2). The left-side case 10L and the right-side case 10R may be releasably secured to remain in the collapsed position, by using, on the case ends opposite from the hinge 110, a twist lock and pivotable plate, similar to the arrangement in U.S. Pat. No. 3,407,454 to Myatt for "Quick Release Fasteners," the disclosures of which are incorporated herein by reference.

Either the left-side case 10L or the right-side case 10R may include a handle that is centrally positioned, and which may be pivotally attached to the case to be able to pivot down and out of the way during a procedure or when storing the organizer case 10, or be able to pivot upwards to be grasped by the practitioner for transporting of the dental implant organizer case 10. Alternatively, a separate handle 25L may be pivotally secured to the left-side case 10L and a separate handle 25R may be pivotally secured to the right-side case 10R of implant organizer case 10. The two handles 25L and 25R may snap together when the case is in the collapsed position, through the use of a post member 25P on one handle, with the post member being received in a recess in the other handle using a friction fit.

Both the left-side case 10L and the right-side case 10R of implant organizer case 10 may include a housing that may be segregated using a plurality of walls (or a single integral multi-flanged feature) to form a series of compartments. Since the prosthodontic surgeon will generally not implant a platform within the upper or lower jaw bone at the site of the wisdom teeth (teeth numbers 1, 16, 17, and 32), both the left-side case 10L and the right-side case 10R of implant organizer case 10 may preferably have seven compartments each, which may be accessible from the top of the case. Left-side case 10L may comprise compartments C2, C3, C4, C5, C6, C7, and C8, for those corresponding tooth numbers, and right-side case 10R may comprise compartments C9, C10, C11, C12, C13, C14, and C15.

Each of these compartments may be adapted to support one or more implant platform vials. To accommodate a "suggested" implant platform size (diameter and length) for a particular site (tooth location), and at least two other platform sizes that may possibly be needed by the surgeon as an alternative (indicated graphically in the figures as 1°, 2°, and 3° platform selections), each of the compartments may include a support member configured to support at least one such vial, and may preferably be configured to support three such vials—vials 100V, 101V, and 102V. Support for a fourth or a fifth alternate vial or even more alternate vials could be similarly accommodated using the support means discussed hereinafter.

Since these vials are typically cylindrical (see FIG. 1), each of the compartments may comprise hollow cylindrical holder members that may protrude upwards from its bottom wall. As seen for the example compartment C2 in FIG. 2C, to support three cylindrical vials, the compartment may have three hallow cylinders, C2$i$, C2$ii$, and C2$iii$ therein. These hollow cylinders may be integrally formed with the compartment's bottom wall, or may alternatively be secured to the bottom wall using any suitable manufacturing method, including, but not limited to, using mechanical fasteners through a flange extending from the cylinder, using an adhesive, by friction welding, etc. The holder member need not be cylindrical, and could alternatively have a square-shaped cross-section to support a cylindrically shaped vial, or a rectangular-shaped vial. For any shaped holder member being used, it may preferably be slightly oversized to provide some clearance with the vial to account for differences in the size of packaging used by various platform manufacturers. In addition, rather than using a form-fitting support member that generally mirrors the cross-sectional shape of the packaging of the platform, vial support may alternatively be provided by a series of wires (3 or more wires), each of which may protrude upwardly from the bottom wall of the compartment, and which may be bent by the oral surgeon or his/her assistant to suitably support the vial's uniquely shaped envelope.

Each of the alternative holder members described herein may preferably be configured to releasably receive and support one or more implant platform vials in an upright position, as seen in the cross-sectional view of FIG. 2C, because the vials typically have, its identifying characteristics labeled upon its top cover, as seen in FIG. 2D. This permits the oral surgeon to glance at the label and verify that the vial containing the proper sized platform is being removed for use at a particular implant site. This upright positioning and suitable spacing between the vials when stored within a compartment also permits the practitioner, or an assistant, to easily grasp and remove the desired vial therefrom. Also, as depicted in FIG. 2C and FIG. 2D, the support provided for the dental implant vials may be such that they may be positioned in-line within the elongated compartment. Also, as seen in FIG. 2F for the three hallow cylinders, C2$iv$, C2$v$, and C2$vi$ therein, the vials may be stored in the upright position at different levels, so that the vial with the preferred implant platform is most easily accessible, the first alternate platform is next most accessible, and so on, which may serve as a visual reminder as to the size preferences.

Figure 1A:
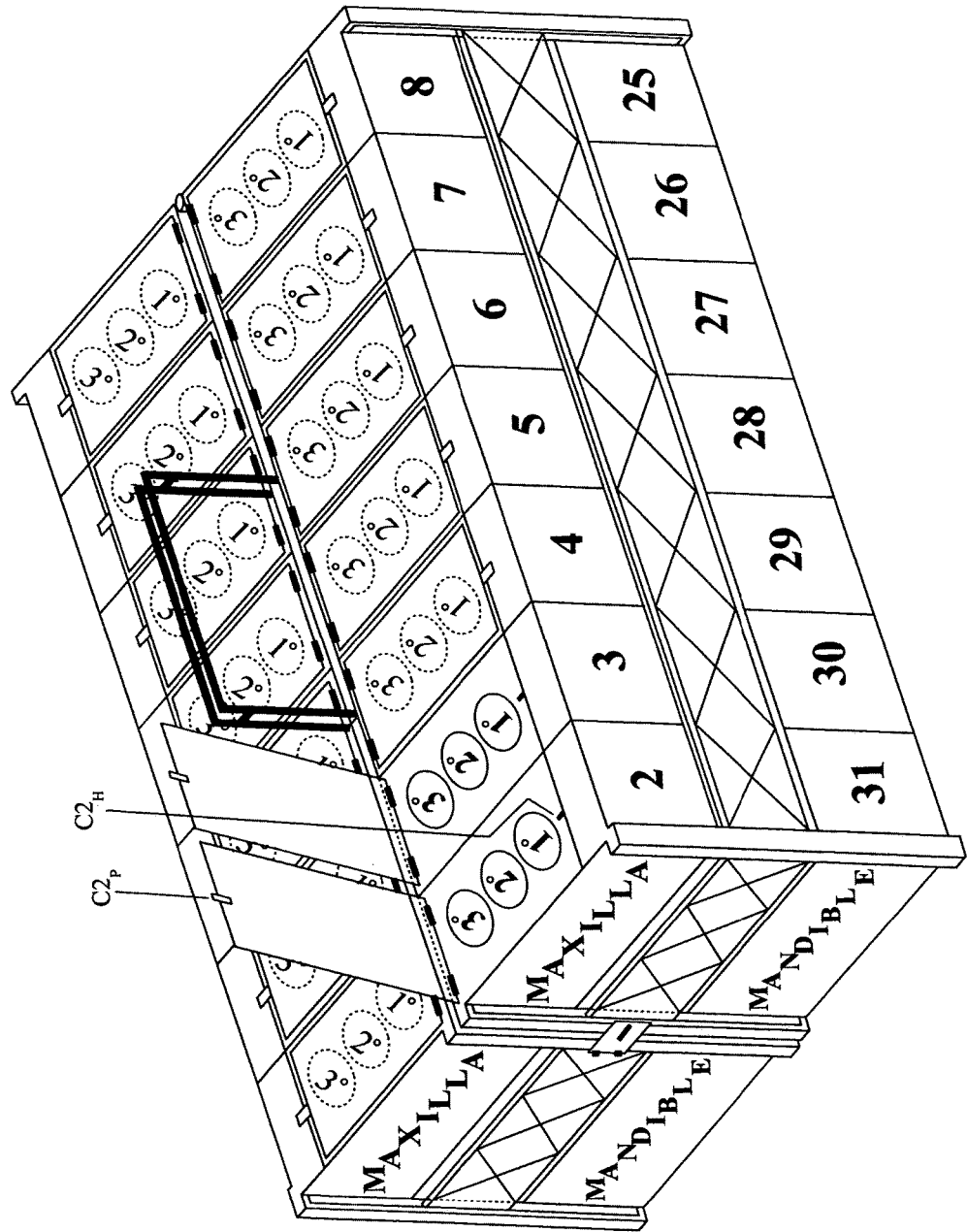
FIG. 1A is the organizer case of FIG. 1, but is shown using a hook material and a loop material for releasably securing of each of the lids in the closed position.
Figure 1B:
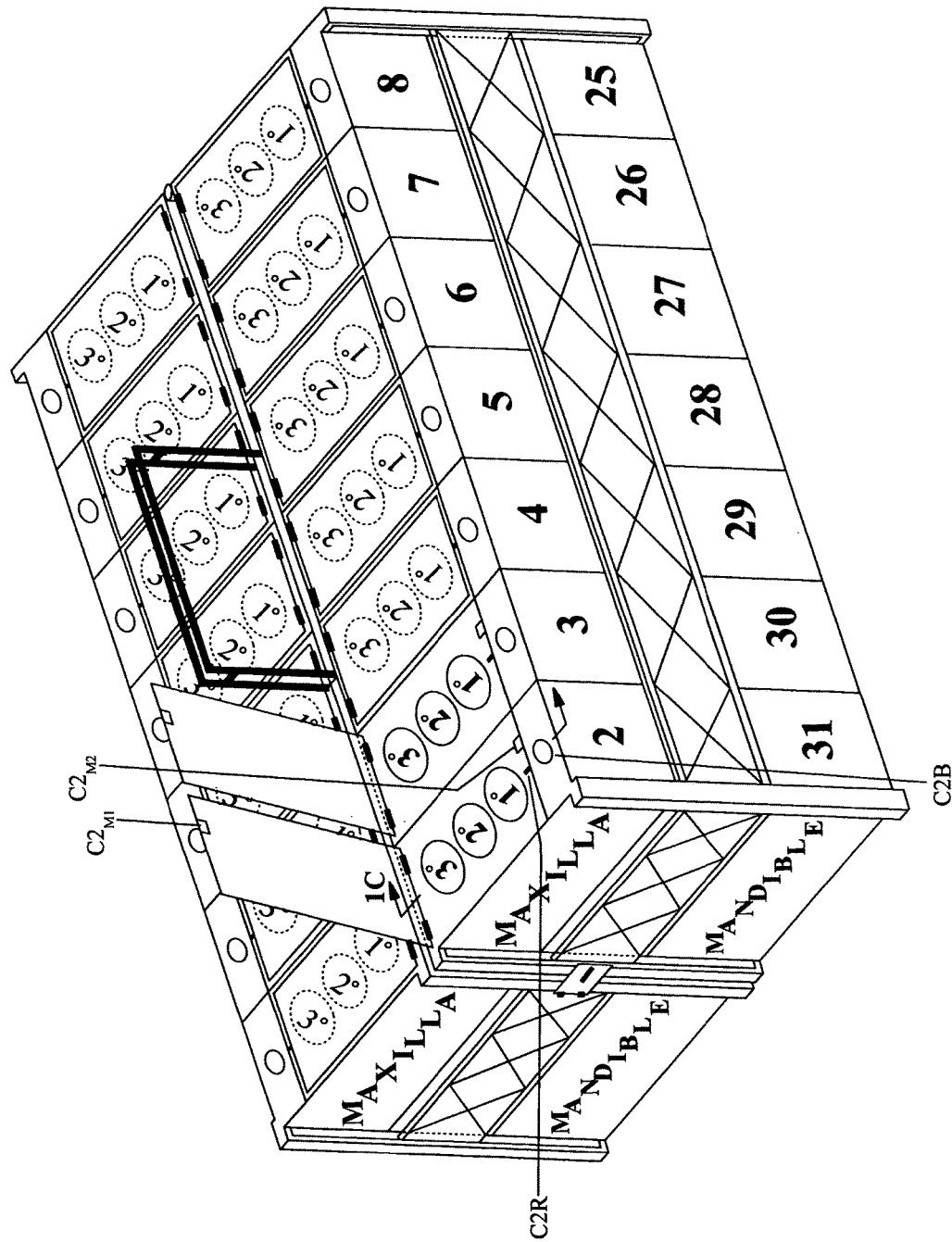
FIG. 1B is the organizer case of FIG. 1, but shown using a first magnet and a second magnet for releasably securing of each of the lids in the closed position.
Figure 1C:
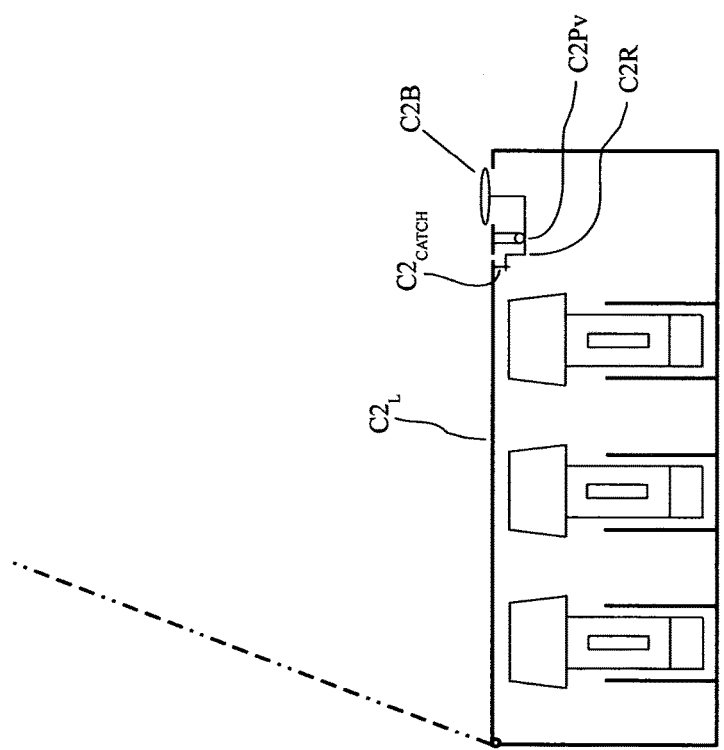
FIG. 1C is a side cross-sectional view showing the rocker arm and the push button for one of the compartments of the organizer case, as seen in the perspective view of FIG. 1B.
Figure 1D:
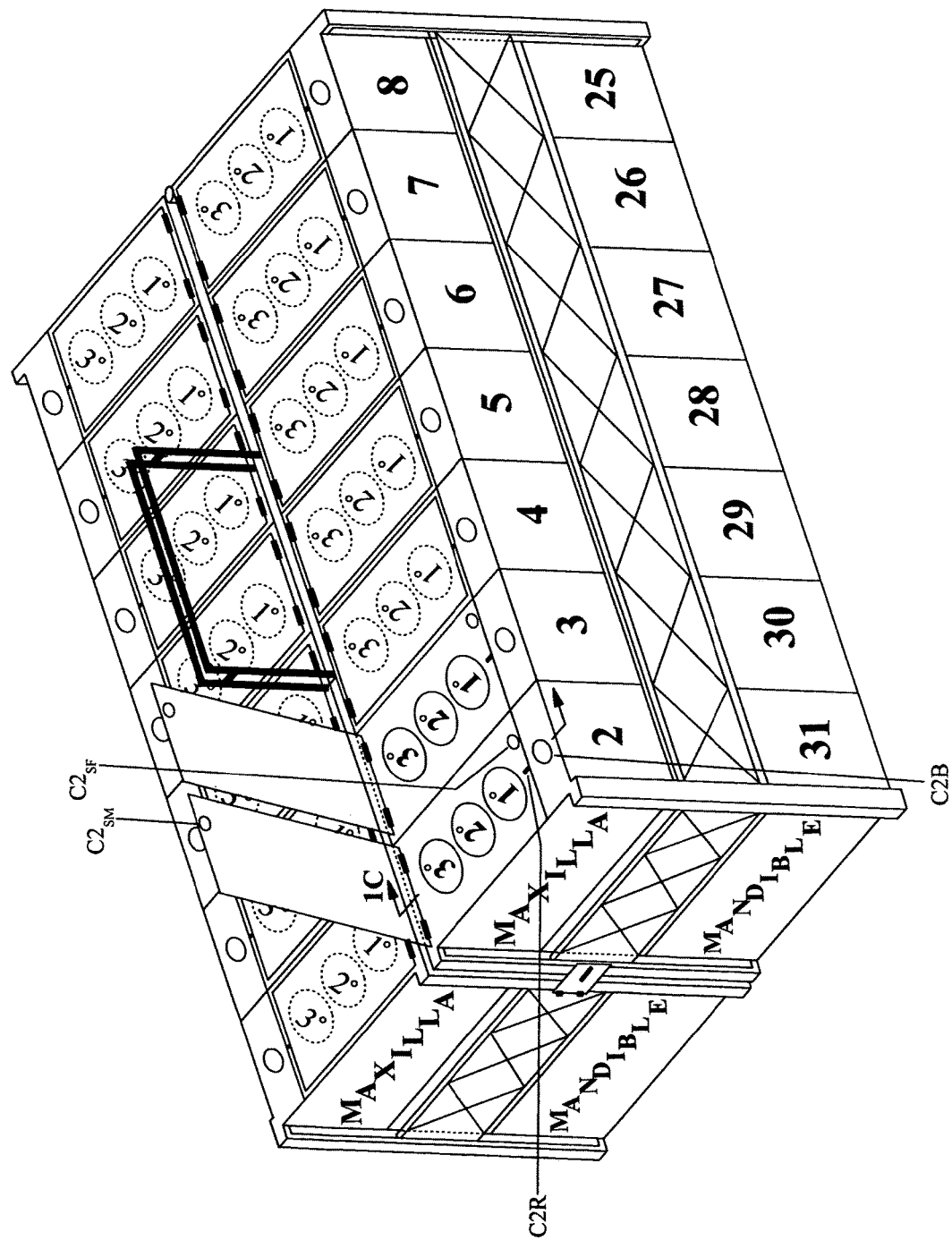
FIG 1D is the dental implant platform organizer case of FIG. 1, but which furter includes a male snap and a female snap that form a snap fastener that may be usable to releasably secure the lid in a closed position.

Each compartment may preferably also have a hinged lid—lid C2L for the compartment C2 in FIG. 2C. The lid may pivot about a hinge that may have a torsion spring (e.g., spring C2$_T$ in FIG. 2), compression spring, or other biasing means thereon that serves to bias the lid from a closed position, in which it retains the vials within the compartment, into an open position, which exposes an opening C2$_{open}$ into a cavity C2$_{cav}$ of the compartment (see FIG. 2F). With the lid in the open position, the oral surgeon may freely access any one of the vials for implantation of the platform contained therein. The hinged lid may be retained in the closed position by any suitable latching means. For example, latching of the lid may be accomplished using a hook and loop fastening fabrics (e.g., hook material C2$_H$ and loop material C2$_P$ for compartment 2 shown in FIG. 1A), which is known by the trade name Velcro®, where a strip or tab of the material may extend beyond the lid to be graspable by the person seeking to separate the hook and loop fabric pieces and open the cover member. The latching of the lid may also be through the use of a snap fastener (e.g., male snap C2$_{SM}$ on the cover of the second compartment, and female snap C2$_{SF}$ on a portion of the framework shown in FIG. 1D), such as the "Fastening Snap" of U.S. Pat. No. 3,975,803 to Katayama, the disclosures of which are incorporated herein by reference. As another example, the lid may have a small magnet on a bottom surface that could overcome the biasing through attraction to a corresponding magnet that is mounted within the compartment or is inset into the frame that supports the lid (e.g., magnet C2$_{M1}$ on the cover of the second compartment, and magnet C2$_{M2}$ on a portion of the framework shown in FIG. 1B). A rocker arm C2R may be pivotally attached at C2PV to the framework that supports the compartment, and may have one end that is connected to a push-button C2B, with the other end being capable of engaging and driving the lid C2L, to thereby separate the magnets, and allow the torsion spring to bias the lid into the open position. The magnet/release arrangement may also be the same as shown by U.S. Pat. No. 4,026,588 to Bisbing for "Push-to-Open Magnetic Catch," the disclosures of which are incorporated herein by reference. Alternatively, instead of a magnet, a mechanical catch C2$_C$ on the lid C2$_L$ may engage the rocker arm, and which may become disengaged therefrom by a user depressing the button C2$_B$ when seeking to open the lid. Rather than a rocker arm, a simple, spring biased, siding member or members may be used to engage the catch on the lid, similar to the latch on a door or on the glove box of a car. As another alternative, the push-to-open arrangement for each of the lids may be the integrally molded plastic hinge disclosed by U.S. Pat. No. 7,497,351 to Amundson for "Wet Wipe Dispensing System."

A lid may only be opened by a practitioner during a procedure for tooth/teeth numbers for which an implant is being placed during the surgery. Each lid may be opaque, or may alternatively be translucent to permit the practitioner or an assistant of the practitioner to recognize that an implant within the case has been utilized for a previous procedure, and that it needs to be replaced before using the case for another procedure.

The upper front of the left-side case 10L may receive a placard or have stenciled thereon, tooth numbers for respective compartments for the teeth of a patient's upper right side, which, in the American system, would principally be teeth numbers: 2, 3, 4, 5, 6, 7, and 8 (wisdom tooth #1 not being included). In the European system (Palmer Notation method) they would be teeth numbers: (UR) 7, 6, 5, 4, 3, 2, and 1. The upper front of the right-side case 10R may receive a placard or have stenciled thereon, the tooth numbers for respective compartments for the teeth of a patient's upper left side, which, in the American system, would principally be teeth numbers: 9, 10, 11, 12, 13, 14, and 15 (UL 1, 2, 3, 4, 5, 6, and 7 in the European system).

In addition, the lower front of the left-side case 10L may receive a placard or have stenciled thereon, the tooth numbers for the teeth of a patient's lower right side, being teeth numbers: 31, 30, 29, 28, 27, 26, and 25 (LR7-1 in the European system). Finally, the lower front of the right-side case 10R may receive a placard or have stenciled thereon, the tooth numbers for the teeth of a patient's lower left side, being teeth numbers: 24, 23, 22, 21, 20, 19, and 18 (LL 1-7 in the European system).

Figure 2B:
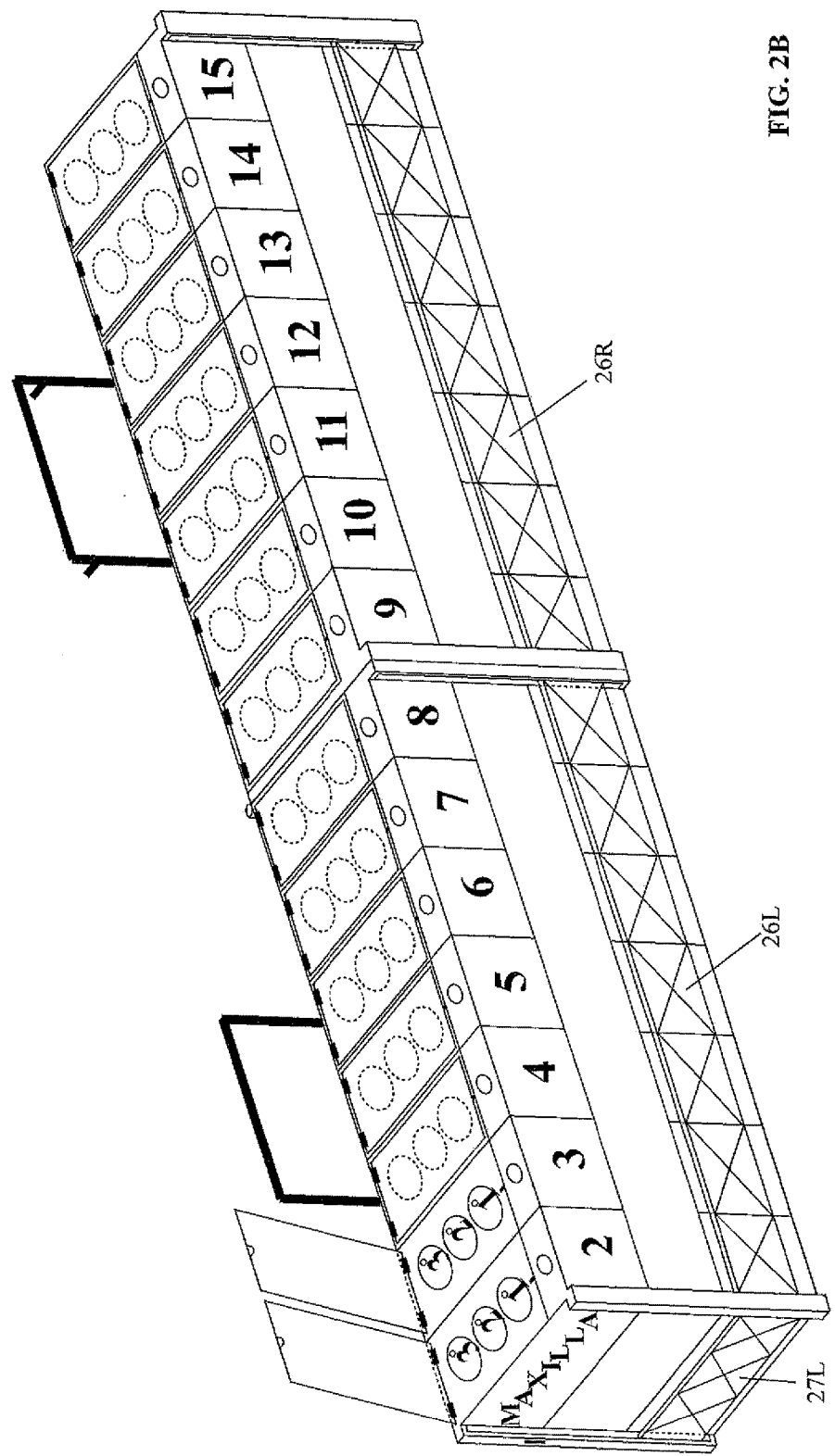
FIG. 2B is the dental implant platform organizer case of FIG. 2, being shown in the extended, in-line position for use during an implant procedure, and with its slidable shields having been slid downward to conceal the mandible tooth numbers during a procedure requiring implants on the patient's maxilla.

A shield 27L may be slidably received on the front of the left-side case 10L, by having the ends of the shield be received in a friction fit in a vertical recess at the first end 10Li and at the second end 10Lii of the left-side case. A shield 27R may similarly be received on the front of the right-side case 10R, by having the shield be slidably received on the front of the case, by having the ends of the shield be received in a friction fit in a vertical recess at the first end 10Ri and at the second end 10Rii of the right-side case. The shields 27L and 27R may thus be slid upward to conceal the teeth numbering for the maxilla, when the case is being used for implants on the patient's mandible (FIG. 2A), or shields 27L and 27R may instead be slid downward to conceal the teeth numbering for the mandible, when the case is being used for implants on the patient's maxilla (FIG. 2B). A placard or stenciling may also appear on the sides of the case identifying the upper numbering as being for the "MAXILLA," while the another placard or stenciling may identify the lower numbering as being for the "MANDIBLE." A slidable shield 27L, located on the first end 10Li of left-side case 10L may be used to similarly conceal the "MAXILLA" stencil when the case is being used for placing implants within the mandible, or vice versa, and a slidable shield 27ll, located on the first end 10Ri of right-side case 10R may be used to correspondingly conceal the "MAXILLA" and "MANDIBLE" lettering thereon.

Figure 2E:
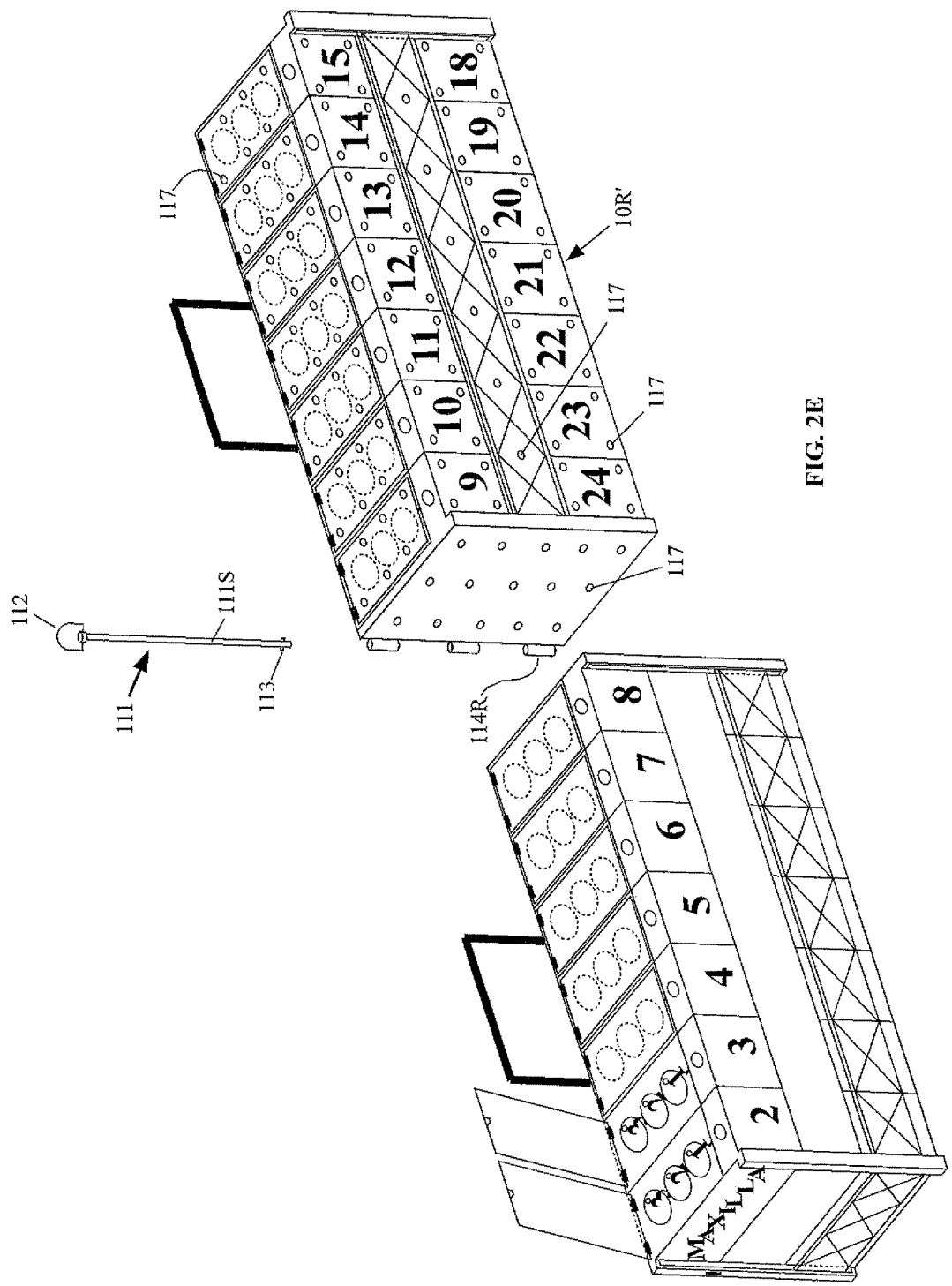
FIG. 2E is an exploded view of the organizer case of FIG. 2.

FIG. 2E is an exploded view that illustrates a couple of different variations of the dental implant organizer case 10. First, the organizer case shown in FIG. 2E may be configured to permit complete separation of the left-side case portion from the right-side case portion. Rather than using the simple hinge pin 110 shown in the previous figures, a hinge pin 111 may instead be used, which may include a ring 112 secured to the head of the pin. In addition, the bottom portion of the hinge pin 111 may include a detent 113. The detent 113 may comprise a pair of opposingly biased spherical balls being retained within a transverse orifice in the shaft 111S of the hinge pin 111, which, once passed through the barrel sections 114R of the right-side case section and through the barrel sections of the left-side case section, are biased outwardly to releasably secure the hinge pin relative to the lowermost barrel section. Additionally, although it is only shown on the right-side case portion 10R', both case portions (left and right) may include a plurality of openings 117, that may be in the sides and back of the case, as well as in the lids of the compartments, and in the shields, to permit penetration therethrough by steam and pressure within an autoclave, to provide for sterilization of the case-portions. Being able to separate the left-side case portion from the right-side case portion, by withdrawing the hinge pin 111 from the barrel sections using the ring 112, better facilitates fitting the organizer case into an office-sized autoclave for sterilization. It should be noted that both the left and right-side case portions with the plurality of openings therein may also be subjected to cold sterilization, which may be per U.S. Pat. No. 4,839,004 to Castellini for "Method and Apparatus for Cold Sterilization of Surgical Instruments, in Particular Dental Surgery Instruments," the disclosures of which are incorporated herein by reference.

Figure 3:
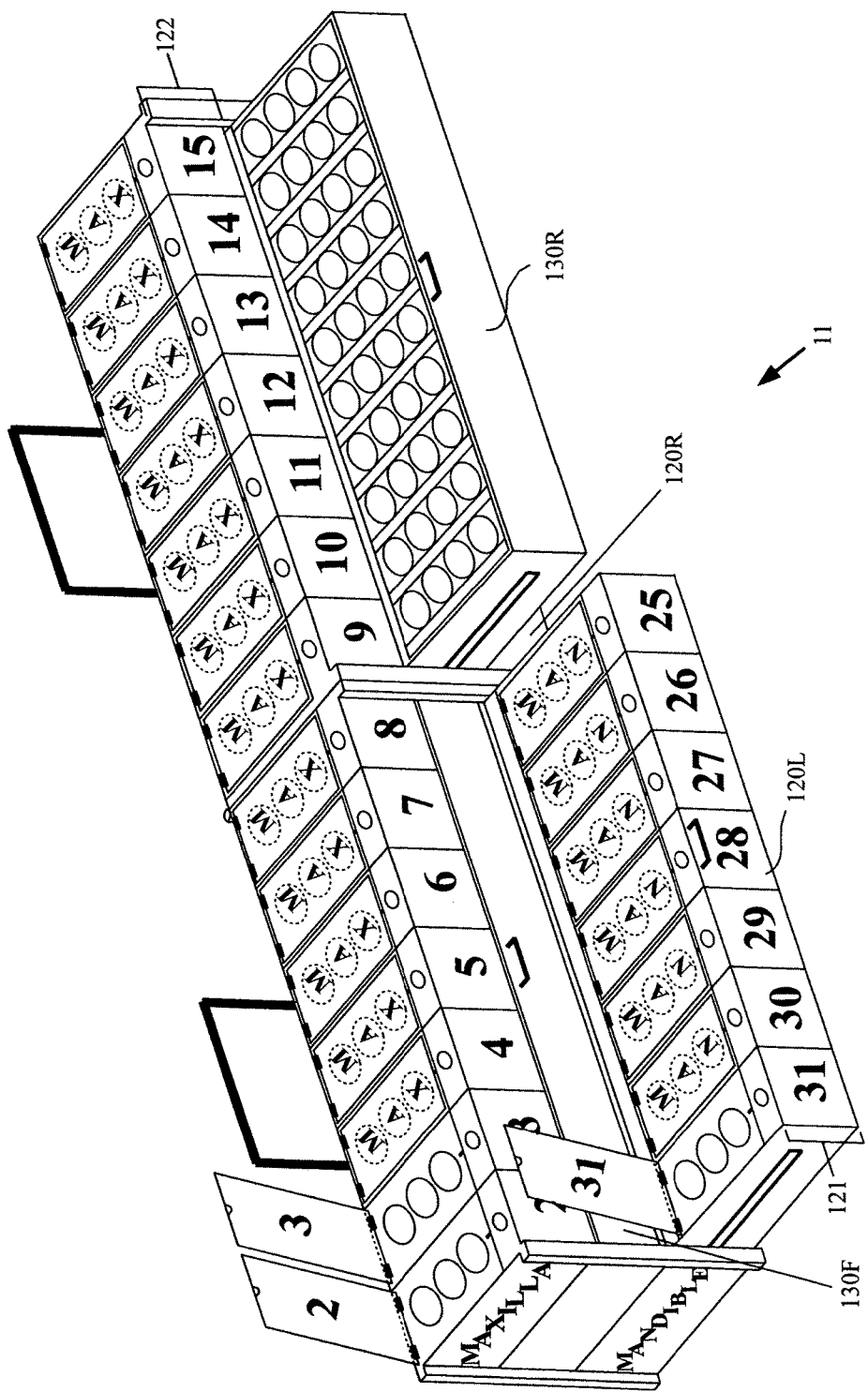
FIG. 3 shows a variation to the dental implant platform organizer case of FIG. 1, and may include a lower set of compartments within a pair of slidable trays, for use during an implant procedure requiring implants on both the patient's maxilla and mandible.

FIG. 3 illustrates another variation of case 10, in the form of dental implant organizer case 11, which may generally be constructed the same as organizer 10, except that the left-side case 10L and the right-side case 10R may each have a respective lower tray, 120L and 120R, which may slide outwardly from the frame. Each lower tray 120L and 120R may also contain seven in-line compartments that may preferably support a number of vials comparable to what is supported by the upper compartments. Therefore, in this embodiment, the upper level of compartments 122, which include the upper left compartments (C2, C3, C4, C5, C6, C7, and C8) and the upper right compartments (C9, C10, C11, C12, C13, C14, and C15) may be dedicated to only organizing/storing vials of implant platforms for the teeth of the maxilla. Also, the lower level of compartments 121, which include corresponding lower compartments (C31, C30, C29, C28, C27, C26, C25, C24, C23, C22, C21, C20, C19, and C18) of the lower trays (120L and 120R), may be dedicated to only organizing/storing vials of implant platforms for the teeth of the mandible. Note that rather than using a slidable tray, the housing for this embodiment may simply be stepped, so that both the upper and lower compartments may simultaneously be exposed all of the time.

In addition, the dental implant organizer case 11, since it may not require the shields utilized with organizer 10, may instead have a center tray 130L on the left-side case 10L and a center tray 130R on the right-side case 10R, with each center tray being slidably received between the upper compartments and the lower tray. Center trays 130L and 130R may have support therein for receiving a closely packed plurality of vials that may be used as replacements for the vials organized and presented within the upper and lower compartments, after they have been used in a procedure. Each slidable center tray may have a protruding handle, or an inset handle. The drawer slides that are used to permit the center trays to slide outwardly may have a detent, in order to normally retain the trays in the closed position.

Stenciling may be provided on the top of the lids for the upper compartment (abbreviated as "MAX") to identify their use for implantation on the maxilla, and for the lower compartments (abbreviated as "MAN") to identify their use for implantation on the mandible. The "MAX" and "MAN" stenciling may serve as an added reminder for the oral surgeon, as to the intended location for those implants (maxilla or mandible), and the tooth number may also be stenciled on the bottoms of the lids for the same reason.

Prior to performing an extensive implant procedure, the oral surgeon or assistant may position the case on a cart in proximity to the surgical chair, and pivot the left-side and right-side cases into the extended, in-line position. The lower trays may then be slid outwardly to expose the lower compartments. To further assist the surgeon during the procedure, the lids of only the tooth locations to receive implants may be unlatched, thereby biasing the lids into the open position. The surgeon will therefore have the correct assortment of tooth-specific implant platforms readily available to him/her during the procedure, along with a textual indication of which implant locations—tooth numbers and jaw position (maxilla/mandible)—that those platforms are intended for, to serve as a visual cue during the procedure to eliminate confusion and to help prevent accidental misplacement of an implant.

Figure 4:
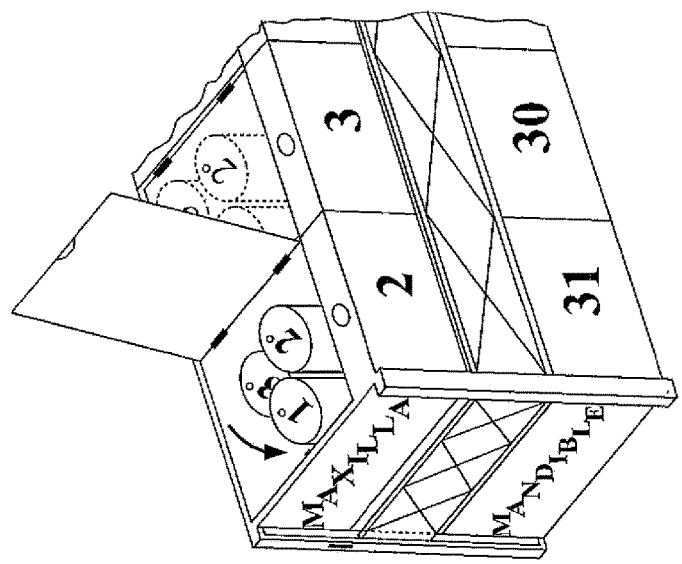
FIG. 4 shows another variation to the dental implant platform organizer case of FIG. 1, and may have the three alternative implant platforms for each tooth location releasably received within a receptacle, with the three receptacles being rotatably mounted upon a lazy Susan.

FIG. 4 shows an alternative vial holder arrangement within the compartments, whereby the holder members for the vials may be arranged in a circular pattern, and may be supported upon a rotatable plate, like a lazy Susan. In addition, the holder member for the vial containing the "suggested" implant size, and the holder members for the vials containing the second and third implant platform choices, may be adapted to provide different upwardly protruding heights for the different vials, such that the "suggested" implant platform protrudes upwardly the most, then the second choice would protrude upwardly the next highest, with the third choice being disposed at the lowest height above the compartment floor. It should also be noted, that for any of the organizer cases disclosed herein, the lids may pivot in any desired direction, including sideways, as illustrated in FIG. 4.

Figure 5:
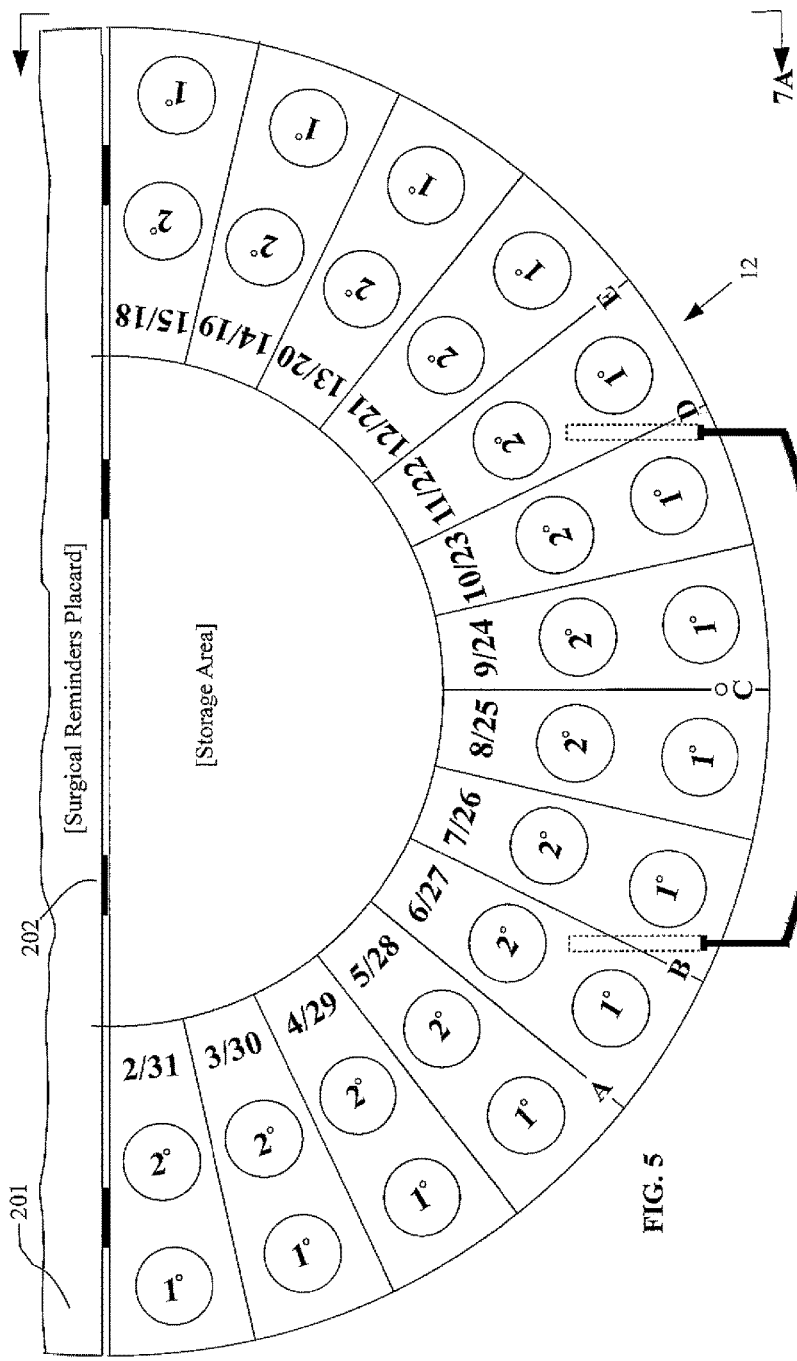
FIG. 5 is a top view of a second embodiment of the dental implant platform organizer case of the current invention, which may be formed into a semi-circular shape to more closely resemble the positioning of the tooth locations in the patient's mouth.
Figure 6:
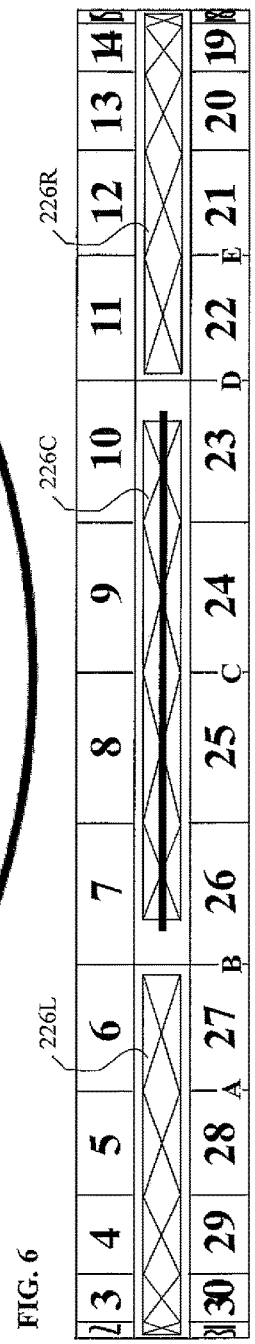
FIG. 6 is a side view of the dental implant platform organizer case of FIG. 5.

FIG. 5 illustrates an alternative organizer case embodiment of the current invention, in the form of dental implant organizer case 12. Dental implant organizer case 12 may have a series of compartments set in a semi-circular arrangement, being oriented similar to the way the teeth in a patient's mouth appear to the oral surgeon. Dental implant organizer case 12 may contain shields 226L, 226C, and 22611 (FIG. 6), similar to those used on organizer case 10. These shields may slide upward or downward, depending upon whether the case is to be used for implants on either the Maxilla or the Mandible. Alternatively, shields 226L, 226C, and 22611 may be eliminated and the semi-circular dental implant organizer case may have two sets of compartments similar to organizer case 11.

Figure 7A:
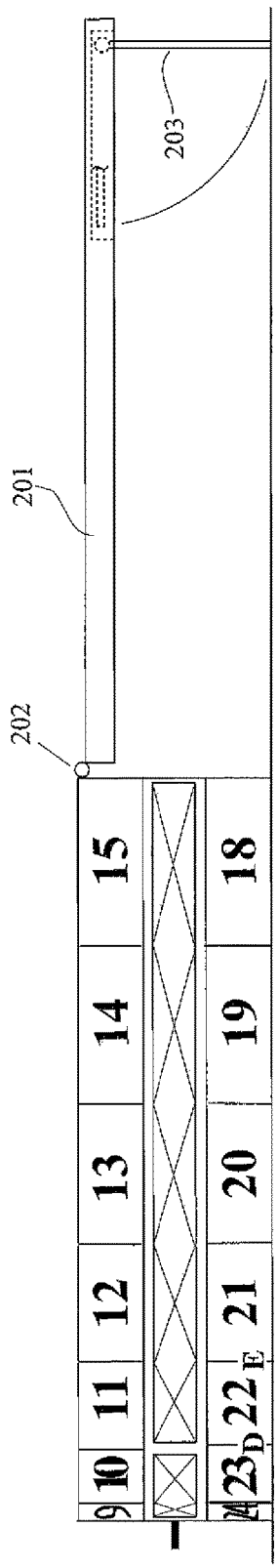
FIG. 7A is a side view of the organizer case of FIG. 5, with the cover shown in the open position.
Figure 7B:
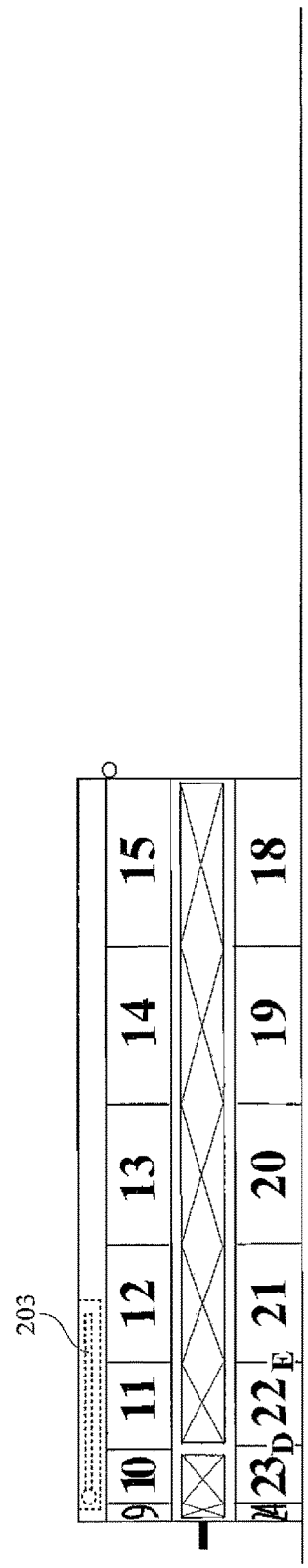
FIG. 7B is the side view of FIG. 7A, but with the cover shown in the closed position.

A case cover 201 may be pivotally attached to the case using hinge(s) 202. The underside of the cover 201 may have one or more placards 250, which may be visible to the oral surgeon during a procedure when the case is opened, and which may provide procedural guidelines and reminders. The interior central portion of the case may be left open to be usable for storage. The cover may be supported in the open position to be generally parallel with the surface upon which the case rests, through the use of stops on the hinge(s) 201 to limit pivotal movement of the cover, or through the use of a support leg 203. The support leg 203 may rotate 90 degrees into an extended position to provide support for cover 201 when the cover is opened, as seen in FIG. 7A, and it may thereafter counter-rotate 90 degrees to return to a retracted position where it is retained within a recess in cover 201, when the cover is closed, as seen in FIG. 7B. In addition to, or as an alternative to, the cover 201, each of the compartments may have a lid pivotally attached to the case to selectively provide access to each compartment, similar to what was illustrated for organizer case 11.

Dental implant organizer case 12 may include a plurality of openings in the sides and back of the case, as well as in the cover and/or lids of the compartments and in the shields, similar to case 10R' in FIG. 2E, so that case 12 may also be subjected to sterilization in an autoclave or to cold sterilization.

Figure 8A:
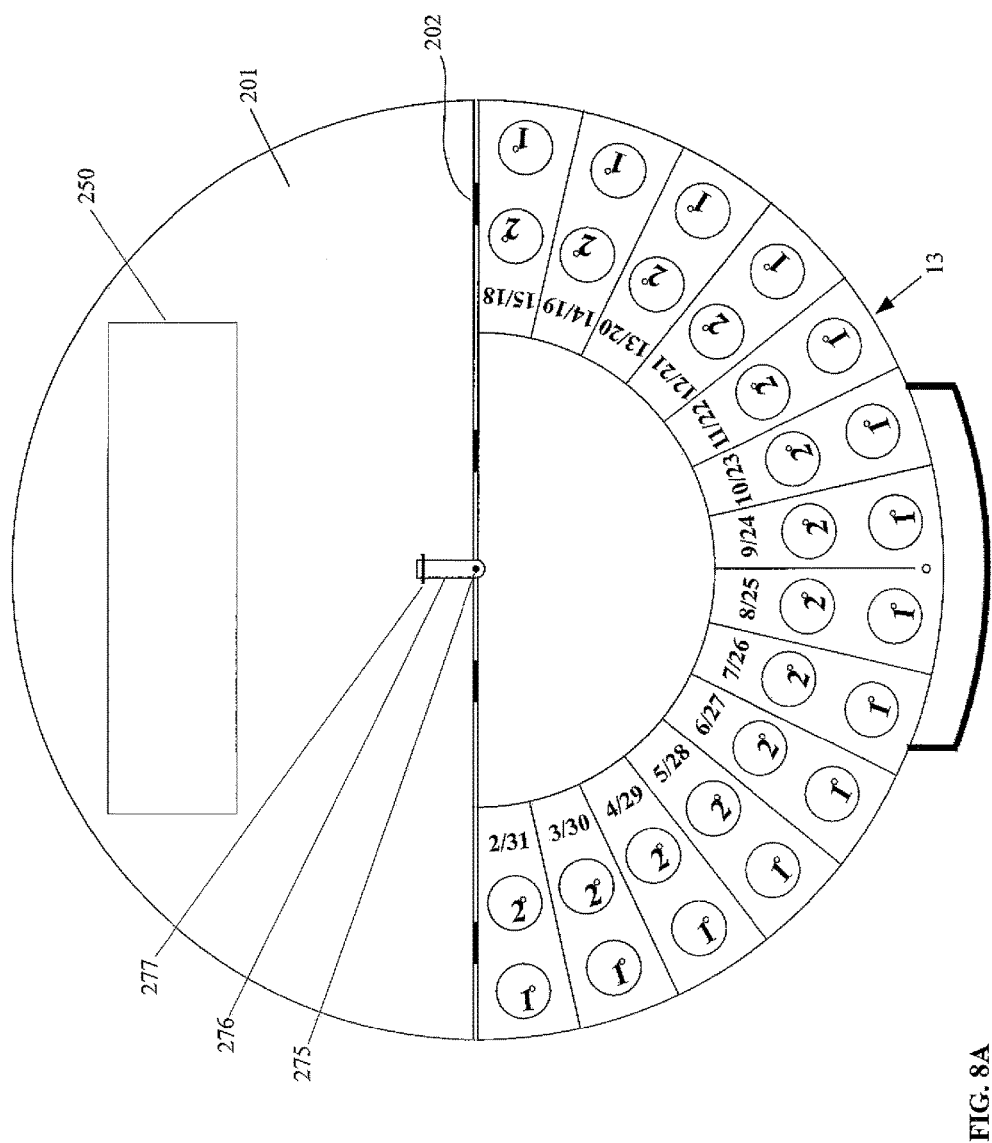
FIG. 8A illustrates a variation of the organizer case of FIG. 5, which provides support for one or more rotator shields that provide selective access to the compartments containing implants for the tooth locations for a particular procedure.

A variation of the semi-circular implant organizer case 12 is shown by organizer case 13 that is shown in FIG. 8A. Organizer case 13 may additionally include a pin 275 that may be usable to pivotally receive rotator shields that may serve to provide selective access to the compartments containing implants for the tooth locations for a particular procedure. The pin 275 may be appropriately secured to the case using any suitable means. The pin 275 may be secured to a strap 276, which may be made of a rigid or flexible material. The strap 276 may be stitched to or hinged to the inside of the cover 201 at 277 to allow the pin to drop into the central storage area when the cover is closed and the case is not in use, or alternatively to allow the pin to be positioned proximate to the center of the semi-circular case when the cover is opened. Where the strap 276 is flexible, stitching may preferably be used at location 277, and where the strap 276 is made of a rigid material, a hinge arrangement at 277 may preferably be used.

Figure 8B:
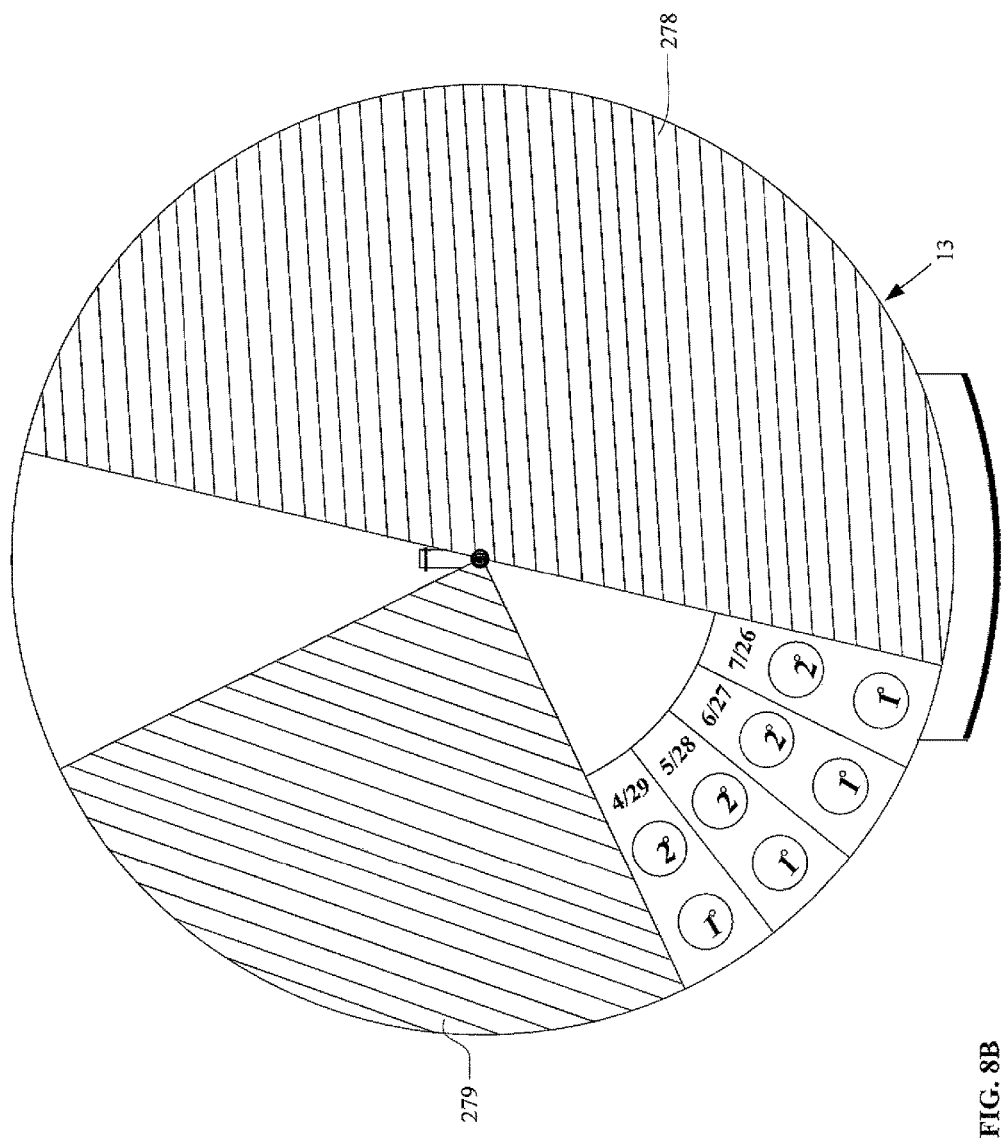
FIG. 8B shows the organizer case of FIG. 8A, with two rotator shields have been received thereon to only permit access to the compartments for teeth numbers 4/29, 5/28, 6/27, and 7/26.

A couple of examples of the rotator shields usable with this embodiment are illustrated in FIGS. 8C, 8D, and 8E. Rotator shield 278 may be a semi-circular shield member that may have a ring 278R secured thereto to be proximate to a center point of the semi-circle. Rotator shield 279 may be constructed to form one-fourth of a circle, and may have a ring or a snap 279S secured thereto to be proximate to a center point of the quarter-circle. The snap may be, for example, the snap member of U.S. Pat. No. 3,975,803 to Katayama. Use of these example shields is illustrated in FIG. 8B. The ring 278R of shield 278 may be received upon the pin 275 to be pivotable thereon. Similarly, where shield 279 comprises a ring, it too may be received upon the pin to be pivotable thereon. Where the snap is used instead of the ring, the snap 279S on shield 279 may be used to releasably secure the shield to the tip of the pin 275 to be rotatable thereon. Use of the snap may also serve to releasably retain any number of pivotable shields upon the pin to better facilitate their pivotal movement, as follows.

The rotator shields may be pivoted to selectively provide access to only those compartments that the oral surgeon will need during a procedure, to avoid errantly utilizing the wrong implant platform at a particular site. For example, where the oral surgeon may be installing platforms at the number 4, 5, 6, and 7 teeth of the Maxilla, The rotator shield 278 and the rotator shield 279 may be positioned as seen in FIG. 8B, so that only those implant platforms will be visible to, and available for the oral surgeon, during the procedure. Small magnets, for example, the magnets 279M on rotator shield 279 seen in FIG. 8E, may be used prevent inadvertent rotation of the rotator shields, once they have been set for the surgery, by their attraction to corresponding magnets on the upper periphery of the case. Where the oral surgeon needs to only implant a platform at a patient's tooth numbers 4, 5, and 7, but not at tooth number 6, the rotator shield 280 seen in FIG. 8E may also be used to block access to the number "6/27" compartment. Rotator shield 280 may thus sweep out an arc segment that is $\frac{1}{14}^{th}$ of a semi-circle to thereby block access to only a single compartment. Other rotators shields may also be conveniently utilized, such as a rotator shield that sweeps out $\frac{1}{7}^{th}$ of a semi-circle, to thereby block access to two adjacent compartments, and/or a rotator shield that sweeps out $\frac{3}{14}^{th}$ of a semi-circle, to thereby block access to three adjacent compartments, etc. The rotator shields may be stacked upon each other using the pin 275.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

What is claimed is:

1. A dental implant organizer case, for use during a dental implant surgical procedure performed on one or more maxillary and/or mandibular teeth of a patient, to selectively provide ready access to two or more elongated containers for each tooth location, each of the two or more elongated containers containing a different sized dental implant platform for the tooth location, with the different sized platforms within the two or more containers usable as a primary implant platform size and one or more alternate platform sizes for the tooth location, said dental implant organizer case comprising:

a housing segregated to form a plurality of elongated compartments, wherein said plurality of compartments comprises fourteen compartments to respectively hold the containers with dental implant platforms to be used for the maxillary teeth and fourteen compartments to respectively hold the containers with dental implant platforms to be used for the mandibular teeth, excluding wisdom teeth, said plurality of elongated compartments being selectively arranged within said organizer case; each said elongated compartment having a respective opening into a cavity therein, and comprising:
a cover member, said cover member being pivotally mounted to said housing and configured to cover said respective opening in a closed position, and configured to be pivotable between said closed position and an open position;
means for latching said cover member in said closed position; and
means for releasably supporting a lower portion of the two or more elongated dental implant containers, to be in-line within said elongated compartment, and to always be in a substantially upright position therein when said case is positioned substantially upright, to expose a label on a top surface of each dental implant container when said cover member is in said open position, and said means for releasably supporting further configured for maintaining the dental implant containers spaced at a discreet distance apart from each other within said elongated compartment; wherein said supporting a lower portion of the containers, said upright positioning, and said discreet spacing between the dental implant containers permits the practitioner to grasp and remove any one of the containers within any said compartment;
and
compartment number identification means, for each of said compartments, said compartment number identification means for said fourteen compartments used to respectively hold dental implant containers for the maxillary teeth being successively numbered, beginning with the number two and ending with the number fifteen for indicating the tooth number for the particular dental implant containers supported within said respective maxillary compartments, said compartment number identification means for said fourteen compartments used to respectively hold dental implant containers for the mandibular teeth being successively numbered with a declining sequence, beginning with the number thirty-one and ending with the number eighteen, indicating the tooth number for the dental implant containers supported within said respective mandibular compartments; each said compartment number identification means being fixedly secured to said housing adjacent to said respective compartment.

2. The dental implant organizer case according to claim 1, wherein said selectively arranged plurality of compartments comprises an in-line arrangement of said compartments.

3. The dental implant organizer case according to claim 1, wherein said selectively arranged plurality of compartments comprises an upper level of compartments for said fourteen compartments configured to support the maxillary dental implant containers, and a lower level of compartments for said fourteen compartments configured to support the mandibular dental implant containers; and wherein said lower level of compartments is formed in a tray, with said tray configured to be slidably received within a portion of said housing.

4. The dental implant organizer case according to claim 3, wherein each said compartment further comprises means for biasing said cover from said closed position toward said open position.

5. The dental implant organizer case according to claim 3, further comprising a handle pivotally secured to said organizer case.

6. The dental implant organizer case according to claim 1, wherein each said cover member comprises a translucent material.

7. The dental implant organizer case according to claim 1, wherein said means for releasably supporting two or more implant containers is further configured to support three or more implant containers at successively different heights within said elongated compartment.

8. The dental implant organizer case according to claim 1, further comprising a second said compartment number identification means, for each of said compartments, each said second compartment number identification means being fixedly secured to an underside of each said respective cover member.

9. A dental implant organizer case, for use during a dental implant surgical procedure performed on one or more maxillary and/or mandibular teeth of a patient, to selectively provide ready access to two or more elongated containers for each tooth location, each of the two or more containers containing a different sized dental implant platform for the tooth location, said dental implant organizer case comprising:
a housing; and
a plurality of walls that form a plurality of elongated compartments selectively arranged within said housing, wherein said plurality of compartments comprises fourteen compartments to respectively hold the containers with dental implant platforms to be used for the maxillary teeth and fourteen compartments to respectively hold the containers with dental implant platforms to be used for the mandibular teeth, excluding wisdom teeth; each said elongated compartment having a first end, and a second end being distal from said first end in said elongated direction, and having a respective opening into a cavity therein, and each said elongated compartment comprising:
a cover member, said cover member being pivotally mounted to said housing to be pivotable between a closed position and an open position, and configured to cover said respective opening in said closed position;
a latch configured to releasably secure said cover member in said closed position;
two or more support members configured to correspondingly and releasably support a lower portion of two or more elongated dental implant containers, to be in-line within said elongated compartment between said first end and said second end, and to always be in a substantially upright position when said case is positioned substantially upright, to expose a label on a top surface of each dental implant container when said cover member is in said open position, and said support members further configured to maintain the dental implant containers spaced at a discreet distance apart from each other within said elongated compartment; wherein said supporting a lower portion of the containers, said upright positioning, and said discreet spacing between the dental implant containers permits the practitioner to grasp and remove any one of the containers within any said compartment;
and
a placard, for each of said compartments, said placard for each of said fourteen compartments used to respectively hold dental implant containers for the maxillary teeth being successively numbered, beginning with the number two and ending with the number fifteen, for indicating the tooth number for the particular dental implant containers supported within said respective maxillary compartments, said placard for each of said fourteen compartments used to respectively hold dental implant containers for the mandibular teeth being successively numbered with a declining sequence, beginning with the number thirty-one and ending with the number eighteen, for indicating a tooth number for the dental implant containers supported within said respective mandibular compartments; each said placard fixedly secured to said housing adjacent to said respective compartment.

10. The dental implant organizer case according to claim 9, wherein each said compartment further comprises means for biasing said cover from said closed position toward said open position.

11. The dental implant organizer case according to claim 10, wherein said latch comprises a snap fastener, said snap fastener comprising a male snap member and a female snap member being fixedly secured to said cover member and to said housing, respectively.

12. The dental implant organizer case according to claim 10, wherein said latch comprises a corresponding pair of magnets, a first magnet of said corresponding pair of magnets being fixedly secured to said cover member, and a second magnet of said corresponding pair of magnets being fixedly secured to said housing.

13. The dental implant organizer case according to claim 10, wherein said latch comprises a rocker arm pivotally attached to said housing, and configured to selectively engage and disengage a catch on said cover member.

14. The dental implant organizer case according to claim 10, wherein each said support member comprises a cross-sectional shape configured to match a cross-sectional shape of the corresponding dental implant container; and wherein each said support member is configured to extend from a bottom of each said compartment into said cavity therein.

15. The dental implant organizer case according to claim 10 wherein said latch comprises a hook and loop fastening arrangement, wherein a first material comprising a plurality of hooks and a second material comprising a plurality of loops are fixedly secured to said cover member and to said housing, respectively.

16. The dental implant organizer case according to claim 14, wherein each said support member is formed with a square-shaped cross-section.

17. The dental implant organizer case according to claim 14, wherein each said support member is formed with a circular cross-sectional shape.

18. The dental implant organizer case according to claim 10, wherein each said support member is configured to support three or more dental implant platform containers at successively different heights within said elongated compartment.

19. The dental implant organizer case according to claim 9, wherein said selectively arranged plurality of compartments comprises an upper level of compartments for said fourteen compartments configured to support the maxillary dental implant containers, and a lower level of compartments for said fourteen compartments configured to support the mandibular dental implant containers; and wherein said lower level of compartments is formed in a tray, with said tray configured to be slidably received within a portion of said housing.

20. The dental implant organizer case according to claim 19, further comprising a second said placard, for each of said compartments, each said second placard being fixedly secured to an underside of each said respective cover member.

* * * * *